Feb. 27, 1940. T. H. WRIGHT Plant Pat. 364
GARDENIA PLANT
Filed Nov. 28, 1938
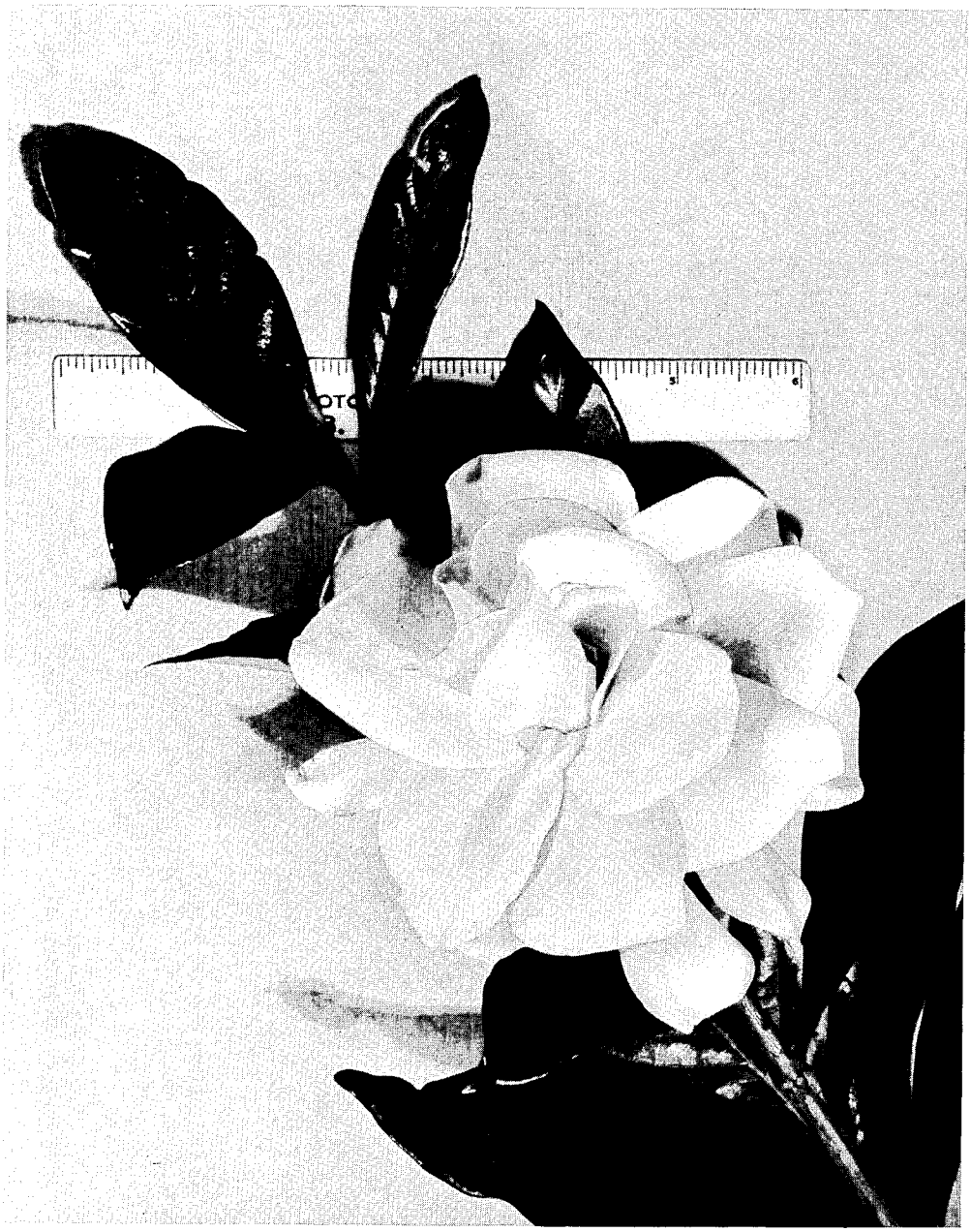
Inventor
THOMAS H. WRIGHT
By Hazard and Miller
Attorneys Patented Feb. 27, 1940

Plant Pat. 364

UNITED STATES PATENT OFFICE

364

GARDENIA PLANT

Thomas H. Wright, Los Angeles, Calif.

Application November 28, 1938, Serial No. 242,740

1 Claim. (Cl. 47—60)

My invention relates to improvements in Gardenia plants, particularly of the type grown in green or hot-houses in many parts of this country for the purpose of sale of the cut flowers to the florist trade and also an object of my invention is to develop a new type of plant which may be sold to greenhouses for reproduction of the flowers. I have found that even good quality strains of Gardenia due in part to the forced manner in which they are grown in greenhouses to produce the flowers for the florist trade, deteriorate and in time substantially revert back to more or less crude plants and flowers. I have introduced a new strain in my Gardenia plants to restore renewed vitality and also to secure better blooms than the former plants I have been marketing and other Gardenia plants of which I have knowledge.

Therefore the first procedures or steps in propagating the Gardenia plant of this application were in the endeavor to produce a hybrid. Very rarely is a Gardenia plant to be found which is fertile but I did find one of the McLellan Grandiflora strain sometimes known as the California Grandiflora. From time to time I fertilized this with pollen from a strain designated Mystery.

The McLellan has been in existence and exploited for many years on the Pacific Coast. The Mystery to the best of my knowledge and belief came from China. Thus by this cross pollenization which was carried out in my greenhouse and nursery at Moneta, California, I succeeded in producing a pod and seeds from which I planted about 100 seeds from which 21 seedlings grew. Of these, only one was worth while propagating. This seedling which was a true hybrid was outstanding in many ways over either of its parents having a larger flower, heavier petals and the leaves more pointed than the foliage of the McLellan type. The foliage in fact was quite similar to that of the Gardenia Mystery.

From this one seedling I reproduced by asexual propagation through the medium of cuttings, successive generations of the plant which continued true to the characteristics of the hybrid. This propagation by cuttings was carried on at my greenhouse and nursery at the place above identified for a sufficient length of time to produce and stabilize the present plant.

Some of the characteristic differences and similarities which are notable of my new plant and its parents, the McLellan and the Mystery, are as follows: The flower differs from the McLellan type in that the outer petals are a little more rounded, the flowers average considerably larger, are more of a pure white and much better keepers when grown under the same conditions. The flower varies from the Mystery in that it has a very short calyx, much shorter than Mystery, the bloom opens what is termed perfectly flat on the plant, this being quite a different shape from Mystery, the bloom is much fuller than Mystery and very seldom shows a center. The petals are also heavier, more in number and the flower is a better keeper. The foliage moreover is closer to the flower than in the Mystery.

As to the growing characteristics, my new plant is a more vigorous grower than either of its parents and for instance a two inch stock planted in the greenhouse in May, grew over four feet high in one year. It is a very heavy brancher and a continuous bloomer. It blooms considerably heavier in the winter time than Mystery and is equally as good as the McLellan, only throwing a greater percentage of larger flowers, many being five to six inches in diameter. The fragrance is of the typical Gardenia character and type but the new plant is more fragent than either the variety Mystery or McLellan. In comparison with other Gardenias with which I am acquainted, the flower is unlike any other variety of which I know at this time, is far superior keeper than other varieties I have grown or observed. The flower holds its color longer both on the plant and when cut. The foliage is a very glossy green, the flowers of pure white and waxy and show more of a rosebud curl effect at the center when open than other varieties. It is one of the best winter producers I have grown, having a very substantial bushy plant with a flower on the end of practically every branch. It also responds well and quickly from a cutting with new flowering shoots. I have found up to the present time, that the plant shows marked resistance to diseases common among all varieties of greenhouse Gardenias, this evidencing that new vigor has been introduced into the plant.

The accompanying illustration is a photograph in black and white showing an opened blossom together with a portion of the stem and a number of the leaves, a measuring rule being shown in the background for comparative measurements. It is to be understood that the illustration of the flower, the stem and the foliage is only intended to present certain of the characteristics of the plant and as these Gardenias are mainly for the purpose of the cut flower trade, the flower is the main element of the illustration. Manifestly, there are differences between the bloom or flowers even growing on the same plant and differences between one plant and another. Therefore the illustration by itself cannot be taken or considered as a positive identification of a similar plant.

The following are some of the more detailed characteristics of the similarities and differences of my present Gardenia of this application in regard to its parent plants.

1. The long, tapering, slightly corrugated leaf is narrower than either of its parents. The axilary vein is light in color, resembling the McLellan type. The petiole, or leaf stalk, is slightly narrower than either the Mystery or McLellan. The Mystery and McLellan leaf widens out closer to the base of the leaf. The Gardenia of this application widens more gradually and the entire leaf is more slender than either of the parents.

The veins of the leaf are substantially the same as the parent plants having usually 13 or 14 veins.

2. Before the flower opens and the bud is still tight and green, it will be observed that it is more pointed than the buds of Mystery or McLellan Grandiflora.

3. The calyx is much shorter on the present Gardenia than on either of the parents. The peduncle is noticeably shorter; and therefore supports the flower in a more upright position on the stalk. The peduncle of Mystery is much longer and rather limber which allows the flower to fall away from the stalk and foliage; while the shorter peduncle of the present Gardenia supports the heavy blossom more firmly on the stalk.

4. The petals of the present Gardenia are pure white of the typical Gardenia tone of color; and are thicker and the veins in the petals are much heavier. The first row of petals of the Mystery, of which there are six or seven, open and curl away from the bud, making it necessary to open the rest of the bud by hand to have an open flower, while the present Gardenia opens naturally and the whole flower flattens out. The center rarely, if ever, shows and the flower will continue to open from the center for several days, unfolding from a tight rose-like center with no pistils or stamens showing. There are six or seven petals in the first row with fifteen to eighteen more petals which unfold from around the tightly wrapped center; and not until the flower is about a week old and yellowing with age do the stamens and pistil show. Even at that age, there may remain additional petals wrapped around the center and when they are forced open with the hand, they will be white. This is an unusual feature in any Gardenia. When the stamens and pistil are disclosed, they differ little from those of any other Gardenia, except that they are shorter and much less in evidence.

5. The color of the leaves, that is the foliage when greenhouse grown to develop a commercial type of flower, is of the typical dark green waxy foliage of Gardenias and practically the same color as that of the Mystery and the McLellan, that is, the parent plants. The typical dark green foliage color depends on supplying the plant with sufficient nitrogen. Should this be insufficient, the leaves will be a lighter green.

6. The stalks in color are substantially the same as the parent plants, Mystery and McLellan, that is, the old hard wood has the same brownish tinge of color and the new green wood practically matching in color that of the parents, when the plant is grown in the greenhouse with the suitable fertilizers.

7. In growing habit my new Gardenia tends to grow straighter than either of the parents however it is manifest that this may be controlled in greenhouse growing by pinching to cause the plants to break from the bottom and produce a good bush plant therefore the characteristics of the growth depend somewhat on the grower and the purpose for which he is developing the plant.

I claim:

A Gardenia plant characterized in being a vigorous grower and showing a marked resistance to diseases common to greenhouse Gardenias, the bud of the flower while tight and green being somewhat pointed, the calyx and peduncle being comparatively short and supporting the open flower firmly on the stalk and in an upright position, the petals of the flower being a pure white and of wax-like texture, opening naturally from the bud and forming a double bloom, the flower continuing to open from the center for several days, unfolding from a rose-like center but maintaining a covering of the pistils and stamen, however when the outer petals yellow with age, there remaining additional inner petals wrapped around the center which when opened being white, the stamens and pistils when thus disclosed being shorter and in less evidence than the stamens and pistils of other Gardenias, the fragance of the bloom being of the characteristic Gardenia odor but more pronounced, the leaf foliage of the plant being a glossy green, the leaf being long and tapering, slightly corrugated and quite narrow, the plant having similarities and differences relative to its parent plants, the Mystery and McLellan all substantially as described and illustrated.

THOMAS H. WRIGHT.